(12) United States Patent
Govorun et al.

(10) Patent No.: US 8,580,535 B2
(45) Date of Patent: *Nov. 12, 2013

(54) MASS SPECTROMETRIC MEASUREMENT OF MICROBIAL RESISTANCES

(75) Inventors: Vadim Markovich Govorun, Moscow (RU); Jochen Franzen, Bremen (DE)

(73) Assignee: Bruker Daltonik GmbH, Bremen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/523,167

(22) Filed: Jun. 14, 2012

(65) Prior Publication Data

US 2012/0264162 A1 Oct. 18, 2012

Related U.S. Application Data

(63) Continuation of application No. 11/743,756, filed on May 3, 2007.

(30) Foreign Application Priority Data

May 9, 2006 (DE) .......................... 10 2006 021 493

(51) Int. Cl.
*C12Q 1/04* (2006.01)
(52) U.S. Cl.
USPC .......................................................... 435/34
(58) Field of Classification Search
None
See application file for complete search history.

(56) References Cited

U.S. PATENT DOCUMENTS

2005/0118650 A1* 6/2005 Dasseux et al. ............... 435/7.2

FOREIGN PATENT DOCUMENTS

| DE | 10038694 A1 | 2/2002 |
| EP | 1299730 B1 | 1/2006 |
| WO | 0244957 A2 | 1/2002 |

OTHER PUBLICATIONS

Walker et al ("Intact cell mass spectrometry (ICMS) used to type methicillin-resistant *Staphylococcus aureus*: media effects and interlaboratory reproducibility" Journal of Microbiological Methods, vol. 48, 2002, 117-126.*
Huff et al "Pyrolysis Mass Spectrometry of Bacteria from Infected Human Urine", Biomedical and Environmental Mass Spectrometry, vol. 13 1986 277-286.*
Arnold et al ("Monitoring the Growth of a Bacterial Culture by MALDI-MS of Whole cells" Analytical Chemistry, 1999 vol. 71, 1990-1996.*
Du, et al., "Identification of *Staphylococcus aureus* and Determination of Its Methicillin Resistance by Matrix-Assisted Lazer Desorption/Ionization Time-of-Flight Mass Spectrometry", Analytical Chemistry, Nov. 1, 2002, vol. 74, No. 21, pp. 5487-5491.
Edward-Jones, et al., "Rapid Discrimination Between Methicillin-Sensitive and Methicillin-Resistant *Staphylococcus aureus* by Intact Cell Mass Spectrometry", Medical Microbiology, vol. 49, 2000, pp. 295-300, The Pathological Society of Great Britain and Ireland.

* cited by examiner

*Primary Examiner* — Jon P Weber
*Assistant Examiner* — Charles Zoltan Constantine
(74) *Attorney, Agent, or Firm* — Robic, LLP

(57) ABSTRACT

Microorganisms, particularly bacteria, are identified and characterized on the basis of a mass spectrometric measurement of their protein profiles with ionization by matrix-assisted laser desorption. In order to measure the microbial resistance to antibiotics, the protein profiles of microorganisms are measured after cultivation for a short time duration in nutrient media containing the antibiotics.

9 Claims, 2 Drawing Sheets

MASS SPECTROMETRIC MEASUREMENT OF MICROBIAL RESISTANCES

BACKGROUND

The invention relates to the identification and characterization of microorganisms, particularly of bacteria, on the basis of a mass spectrometric measurement of their protein profiles with ionization by matrix-assisted laser desorption. Many types of microorganism (also termed microbes below), especially bacteria and unicellular fungi, can be very easily identified mass spectrometrically using a recently discovered method in which small quantities of microbes from a colony cultivated in the usual way on a nutrient medium are transferred to a mass spectrometric sample support plate, where they are measured directly with a mass spectrometer. The mass spectrum particularly represents the proteins of different masses if they are present in sufficient concentration in the microbes. Spectral libraries with hundreds or thousands of microbe spectra are then used to establish the identity of the microbes from this microbial protein profile.

The nutrient medium is usually in a moist gelatin in a Petri dish, thus making it possible to cultivate strains, each of which is pure, in separate microbe colonies simply and in the completely normal way. A quantity of microbes is transferred with a small spatula from a selected colony onto the mass spectrometric sample support, where the microbes are sprinkled with a solution of a conventional matrix substance for ionization by matrix-assisted laser desorption (MALDI). The organic solvent penetrates into the microbial cells and destroys them. The sample is then dried by evaporating the solvent and hence the dissolved matrix material crystallizes. Soluble proteins and peptides and, to a lesser extent, other substances of the cell are thus embedded into the matrix crystals.

The matrix crystals with the embedded analyte molecules are then bombarded with flashes of laser light in a mass spectrometer, thus creating ions of the analyte molecules which can then be measured separately according to the mass of the ions in the mass spectrometer. It is preferable to use time-of-flight mass spectrometers for this purpose. The mass spectrum is the profile of the mass values of these peptide ions, protein ions and other analyte ions. This profile is very characteristic of the types of microbe in question because each type of microbe produces its own, genetically predetermined proteins, each having characteristic masses. The protein profiles are characteristic of the microbes in the same way that fingerprints are characteristic of humans. Many laboratories, including central, state-controlled institutions for disease monitoring and prevention, are working on reliable and legally applicable (so-called "validated") mass spectrometric libraries of protein profiles of microbes.

This simple method can even be used to distinguish between closely related sub-strains of microbes since the proteins of the microbes are genetically predefined and vary clearly in the sub-strains. Slight changes in the genetic blueprint create proteins with a necessarily different structure, whose masses are different to those of proteins whose structure has not been genetically modified; they thus have a different protein profile. New taxonomic classifications of microbes can even be performed in this way.

The masses of the proteins of completely identical types of microbe are naturally always the same and thus strictly reproducible; the intensities of the protein signals, on the other hand, can only be reproduced approximately. The use of different nutrient media for the cultivation affects the metabolism of the microbes and hence affects the quantities of the different proteins which are produced and their intensity in the protein profile. The effect is not great, however. The intensity fluctuations do not interfere with the identification if the computer programs are adapted accordingly.

Likewise, the degree of maturity of the colonies only affects the intensities of the protein signals with respect to each other in the mass spectra, but here, as well, the effect is only slight. Mass spectra which have different characteristics for the same type of microbe only really exist in the case of spore-forming organisms: the spores have protein profiles which are different to those of normal cells.

The computer programs for searching libraries by comparing spectra take account of intensity fluctuations; the intensities play only a minor role here. Current analyses have shown that the identification of the microbes with these programs appears to be very reliable. The programs operate only via the similarity of the mass spectra, without individually identifying the proteins involved; the masses are rigorously incorporated into the search for similarities, the intensities much less rigorously. In particular, it is even possible for several proteins to be missing from the mass spectra (very low intensity) without this interfering with the similarity determination: It suffices for the identification that the mass values for the majority of proteins match. The library spectra are also able to store information as to which protein signals definitely have to be present, for example by storing threshold values for the intensities.

The above, briefly described method of using a small spatula to spread some microbes from a colony onto a reserved spot of a mass spectrometric sample support, which is then sprinkled with a matrix solution, is the simplest and, as yet, fastest type of sample preparation. The method can also be automated with the help of image recognizing pipetting robots for use in routine laboratories. After cultivating a colony which is only just visible, it takes only one or two hours until the identification is complete even if hundreds of samples are analyzed at the same time. Mass spectrometric sample supports each holding 384 samples are commercially available; scanning these mass spectra takes around one to two hours. If the task is urgent, individual microbe samples can be identified in a few minutes.

Other methods of sample preparation such as extracting the proteins after ultrasonic destruction (sonication) of the microbes, or centrifugal extraction have also been investigated. These methods provide spectra which are without exception surprisingly similar.

Nowadays, the mass spectra of the microbe proteins are scanned in linear time-of-flight mass spectrometers because these have a particularly high detection sensitivity, although the mass resolution of the spectra and the accuracy of the masses are considerably better from time-of-flight mass spectrometers with reflectors. In reflector mode, only around a twentieth of the ion signals appear, however, and the detection sensitivity is one to two orders of magnitude worse. The high sensitivity of the linear mode of a time-of-flight mass spectrometer is due to the fact that not only the stable ions are detected but also the fragment ions from so-called "metastable" decays of the ions. Even the neutral particles which are created en route from ion decays are measured. All these fragment ions and neutral particles, which have originated from one species of parent ion, have the same speed as the parent ions and thus arrive at the ion detector at the same time. The arrival time is a measure of the mass of the originally undecayed ions.

The increased detection sensitivity is so crucial for many applications that many of the disadvantages of the linear mode of operation of the time-of-flight mass spectrometer are tolerated. The energy of the desorbing and ionizing laser is increased for these applications, something which increases the ion yield but also increases their instability, although this does not matter here.

Acquiring mass spectra with time-of-flight mass spectrometers generally requires that a very high number of individual spectra are measured in rapid succession, said individual spectra usually being added together measurement point by measurement point to form a sum spectrum. The ions for each individual spectrum are generated by one laser bombardment for each spectrum. The sum spectra have to be generated in this way because of the low dynamic range of measurement in the individual spectrum. A minimum of approx. 50, in some cases even 1,000 or more individual spectra are measured here; in general, a sum spectrum consists of several hundred individual spectra, which modern mass spectrometers measure and add together in a few seconds. The total duration of a sum spectrum acquisition depends on the number of individual spectra and the bombardment frequency of the laser used. Lasers with 20 to 200 hertz are now used for this purpose; it takes around two to 20 seconds to acquire a good sum spectrum.

In the above-described fields of application, mass spectra are measured which reach into high mass ranges of 20,000 Daltons, for example. As previously mentioned, the low mass resolution means that in most parts of the mass spectrum it is no longer possible to resolve the isotope groups, which consist of ion signals which each differ by one Dalton. It is thus only the envelopes of the isotope groups which are measured. Mass spectrometric measuring methods have also become known which provide a higher resolution and a higher mass accuracy; it is not yet known, however, if they achieve comparable sensitivities.

This method of quickly and simply identifying microbes can be used in many areas, for example for monitoring drinking water or quality control in food production. In the case of food production, it is the type of microorganisms present which determines if the food is safe to consume. Suffice it here to mention harmful staphylococci, streptococci and salmonellae, which have to be found by continuous controls. On the other hand, beer, wine, cheese and yoghurt cannot be produced without the beneficial deployment of billions of microbes. The crucial thing here is that the strains are pure.

Strict monitoring is also necessary in the medical field. The main thing is to keep infective pathogens away from hospitals. Constant monitoring and identification of the ubiquitous microbes is a mandatory legal requirement for operating rooms, for example.

The identification of microbes is particularly important with infectious diseases. It is important that the type of pathogen can be identified very quickly in order that the correct medical care can be provided immediately. Mass spectrometric identification has also proven successful here although it has not yet become established.

In the medical field, there is not only the problem of fast identification, but also the problem of identifying resistances to the commonly used antibiotics. It is not possible to fight the disease quickly if the resistances are unknown. What is therefore required is not only fast identification but also fast determination and characterization of the resistances of microorganisms.

Until now, the determination of the resistances has been predominantly based on cultivation experiments of the microorganisms in different nutrient media containing bactericides or other antibiotics. These experiments are protracted and labor-intensive. They take at least 24 hours, usually even two days. Experiments are currently being carried out to identify the resistances using analyses of DNA sequences in the plasmids of the bacteria. The resistances are coded in the plasmids. This type of analytical method is very promising, but has not gained acceptance as yet.

The problem of microorganisms being resistant to antibiotics such as bactericides or fungicides is becoming more and more critical as time goes on. On the one hand, the speed with which microorganisms form resistance to different types of antibiotics is increasing; on the other hand, fewer and fewer new antibiotics with a medical application are being developed. It is now known that the resistances are not formed by new types of mutation and their selection, but by the interchange of plasmids between microorganisms, even between different types of microorganism. The microorganisms infect each other with the resistances.

There are many reasons for the rapid increase in resistances: irresponsible prescribing of antibiotics even when they are not necessary; courses of treatment with bactericides which are rashly broken off before the infective agents have been completely eradicated; irresponsible use in agriculture and livestock farming, often as a purely preventative measure. All these types of behavior help the selection of resistant types of microbes over the non-resistant types.

On the other hand, fewer and fewer new antibiotics are being developed.

Since many new antibiotics have to be taken off the market after only a short time because they became ineffective, it is becoming less and less viable for the pharmaceutical companies to invest large amounts of money in developing antibiotics when this is becoming more and more difficult. According to the WHO, only three new antibiotics have come onto the market since 1990, whereas there were ten between 1940 and 1950 and five between 1971 and 1980.

Since the discovery of antibiotics by Alexander Fleming in 1929 (penicillin), well over 2,000 different types of antibiotic substance have been discovered, although the toxicity and side effects of many of them mean that only around 30 are used widely as chemotherapeutic drugs. The most effective antibiotics are frequently artificially produced derivatives of natural vegetable (from fungi and algae) or animal antibiotics; completely synthetic antibiotics are also available. Antibiotics act in very different ways: Some antibiotics positively destroy the microbes; others lead to the "quiet" death of the cell whereas others are only growth inhibitors and leave the combating and destruction of the inhibited, and hence weakened, microbes to the healing immune system of the patient concerned, whether human, animal or plant.

In the middle of the last century, antibiotics were acclaimed as the great hope for fighting infectious diseases, whereas they are now threatening to quickly become a blunt instrument. The only hope of salvation is through targeted use with courses of treatment which are completed in full, and this requires rapid identification of the infective pathogens and also the fast identification of their specific resistances to various types of antibiotics.

SUMMARY

The invention is based on the mass spectrometric measurement of the modification of the protein profile effected by antibiotics during a brief growth phase in a good nutrient medium under conditions which are otherwise ideal. It is preferable if liquid nutrient media are used since they enable the microbes to multiply quickly, at any rate faster than they would on the surface of a gelatinous medium. The effect of the antibiotics can generally be measured clearly after only around two hours. To give an example, bacteria divide every 20 to 30 minutes; in two hours they can multiply by factors of between 16 and 64.

After the period allowed for the antibiotics to act, the microbes are separated from the nutrient medium by filtration or preferably by centrifuging, applied to a mass spectrometric sample support, sprinkled with matrix solution and fed to the mass spectrometer when dry. The mass spectra measured here can be compared with spectral libraries which also contain the mass spectra of resistant and non-resistant microbes after antibiotics have acted on them. But it is often sufficient simply to compare them with the mass spectra of microbes cultivated in the same way but without being subjected to the effect of antibiotics.

If the antibiotics have a destructive effect on the microbes, then the difference between resistant and non-resistant microbes can easily be seen in the mass spectrum (and can also be determined by computer programs). The situation is different when the microbes simply die off without their proteins being destroyed or greatly changed (something which seldom occurs, however), or when the growth of the microbes is simply disrupted and they remain alive in the nutrient medium but do not multiply further. In such cases, reactive substances can be added to the nutrient media containing antibiotics, said substances boosting and assisting the effect of the antibiotics. It is possible, for example, to add enzymes which can attack and destroy microbes whose growth has been affected while unaffected microbes cannot be attacked by the enzymes.

Alternatively, substances can also be added to the nutrient media which highlight the difference between newly grown and growth-inhibited microbes mass spectrometrically. It is possible, for example, to add isotope-marked nutrients which bring about a characteristic modification of the mass profile of the proteins. If the growth of the microbes is inhibited and they absorb no nutrients, this is immediately identified mass spectrometrically because the modifications are absent.

Adding the same quantity of reference microbes of a similar type and using a quantitative reference measurement can also serve to identify growth-inhibited or even dead microbes, but not those which are lyzed. In two hours, the difference between the number of non-growing and growing microbes has increased by at least a factor of 10 and so it is possible to identify growth-inhibited microbes because there are fewer of them in the mass spectrum.

The method can be used on several portions of the nutrient medium which are used in parallel and supplied with different types of antibiotic in such a way that several types of resistance can be measured at the same time, for example in microtitration plates which can also be centrifuged. Responsible hospitals generally only use between three and a maximum of five antibiotics on a regular basis, with some five further antibiotics on hand for cases of resistance, so that only the resistances to ten antibiotics have to measured on a regular basis.

DETAILED DESCRIPTION

While the invention has been shown and described with reference to a number of embodiments thereof, it will be recognized by those skilled in the art that various changes in form and detail may be made herein without departing from the spirit and scope of the invention as defined by the appended claims.

Figure 3:
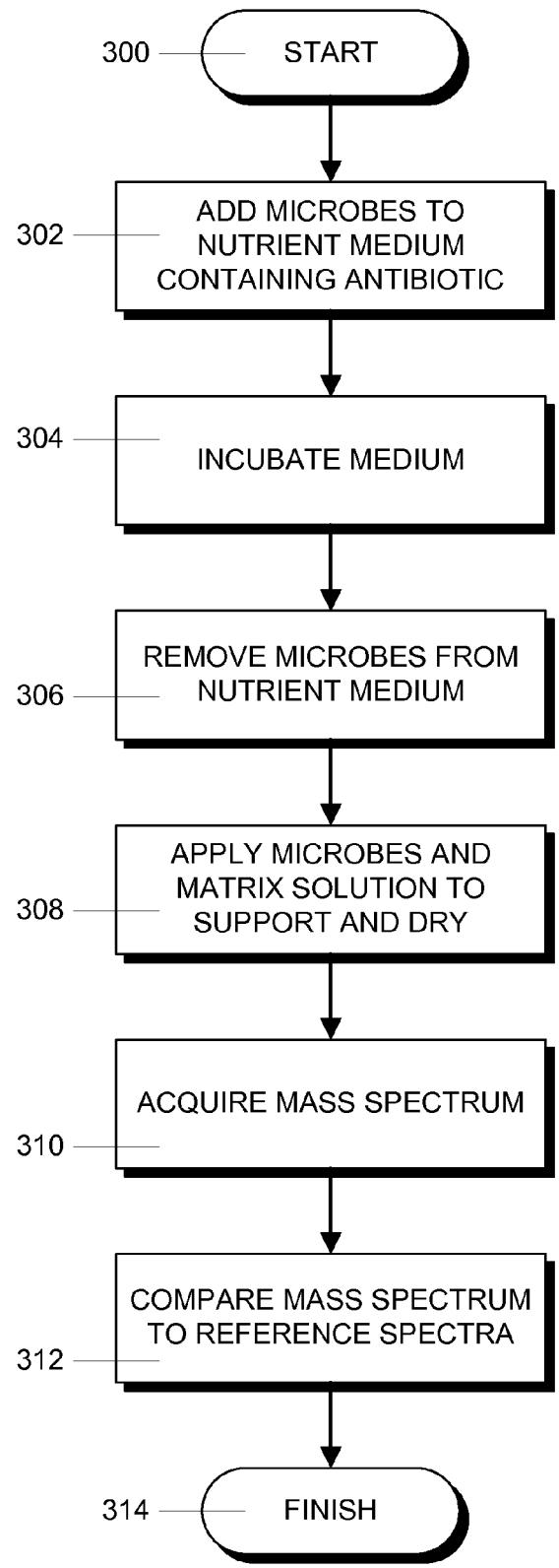
FIG. 3 shows a flowchart illustrating the steps in an illustrative process for determining the resistance of microbes to a specific antibiotic in accordance with the principles of the invention.

As illustrated in FIG. 3, the invention provides a method of determining the resistance of microbes to a specific antibiotic. The illustrative method starts in step 300 and comprises the following steps:
(a) In step 302, a quantity of microbes under investigation is added to a nutrient medium which also contains a quantity of the antibiotic,
(b) Next, in step 304, the microbes are incubated at a predetermined temperature for a predetermined length of time, preferably not longer than a few hours,
(c) In step 306, the microbes are then removed from the nutrient medium by a suitable means, such as centrifuging,
(d) The microbes are then applied, in step 308, together with a matrix solution to a mass spectrometric sample support and the matrix solution is dried on the sample support to form a sample,
(e) In step 310, a mass spectrum of this sample is acquired, and
(f) Then, in step 312, the acquired mass spectrum is compared with reference mass spectra of these microbes. The process then finishes in step 314.

The invention is thus based on the mass spectrometric measurement of the modification of the mass spectrum of these microbes effected by antibiotics during a relatively brief growth phase in a good nutrient medium under conditions which are otherwise as ideal as possible. The mass spectrum essentially represents the profile of the soluble proteins in the interior of the microbes; the non-soluble membrane proteins of the microbes are generally not visible. It is also quite possible that some substances which are not proteins are represented in the mass spectrum; for the sake of simplicity, however, the term "protein profiles" will be used below, said profiles being represented in the mass spectra of the microbes.

The method generally begins with an identification of the microbes, as described above: microbes are cultivated on gelatinous nutrient media and a portion of the microbes of a colony is used to identify the microbes by means of their mass spectrum. This identification is not absolutely necessary, but it can be helpful for the subsequent determination of the resistances according to this invention because it may modify the measurement of the resistances depending on the type of the microbes. It can determine the temperature which must be maintained for optimum growth in the nutrient medium, for example.

Since the parallel identification of a large number of microbes by acquiring the many mass spectra takes around two hours, this time can be used to multiply the remaining microbes from the selected colonies by incubation. It is preferable to use liquid nutrient media since they enable the microbes to multiply quickly. This type of reproduction is generally much quicker than cultivating the microbes on the surface of a gelatinous nutrient medium. Bacteria in a good liquid nutrient medium at optimum temperatures, for example, divide every 20 to 30 minutes, so that in two hours, they can multiply by factors of between 16 and 64. The liquid nutrient media are commercially available.

Further portions of the colony or portions of the microbes of the colony which have been multiplied by incubation can then be used to determine the resistances to different types of antibiotic by incubating them in nutrient media to which the prescribed antibiotics have been added. Here, as well, it is preferable to use liquid nutrient media. The microbes of a colony, which have multiplied in the meantime by being incubated in liquid nutrient media, can be easily distributed over a dozen or so vessels by simple pipetting, said vessels containing the liquid nutrient media together with antibiotics. The effect of the antibiotics can generally be clearly measured after approximately two hours. It is particularly favorable if one of the vessels contains no antibiotic; it is then very easy to obtain a reference mass spectrum for the purposes of comparing microbes which have the same history. This is particularly favorable if a spectral library with corresponding reference mass spectra cannot be used, or if these microbes could not be identified in the spectral library because it did not contain a corresponding reference mass spectrum.

Infectious microbes are incubated for about two hours at temperatures of between 35° C. and 40° C. in the presence of the antibiotics. This temperature is the optimum one for most infectious microbes because they are generally adapted to a life in mammals. Other types of microbes grow best at other temperatures, so it is favorable to identify the microbes beforehand. The microbes are then separated from the nutrient medium, preferably by centrifuging, and are precipitated as sediment. This process of cultivation and removal can be carried out for several antibiotics in parallel in the microvessels of microtitration plates, and the centrifuging can also be done in these microtitration plates. Alternatively, the microbes can also be separated off by filtration or other suitable separation methods.

As is the case with the identification, the separated microbes are then applied to a mass spectrometric sample support, sprinkled with matrix solution and fed to the mass spectrometer when the matrix substance has dried and crystallized out. Matrix solution can also be added directly to the sediments after the supernatants have been removed, the matrix solution being pipetted onto the mass spectrometric sample support with the proteins taken up.

It is preferable if the mass spectra measured in the mass spectrometer are compared with spectra in spectral libraries which also contain the mass spectra of resistant and non-resistant microbes after antibiotics have acted on them. These mass spectra can each contain further information such as threshold values for the protein signals which have to be achieved. However, there is generally such a dramatic difference between the mass spectra of resistant and non-resistant microbes that it suffices just to compare them with the mass spectra of microbes cultivated in the same way but without being subjected to the effect of antibiotics.

The antibiotics can act on the microbes in a variety of ways: They can completely destroy them ("lysis"), they can kill them off without destroying the cell membrane, or they can simply inhibit their growth so that they can practically no longer multiply. The microbes whose growth is inhibited are generally considerably weakened.

Figure 1:
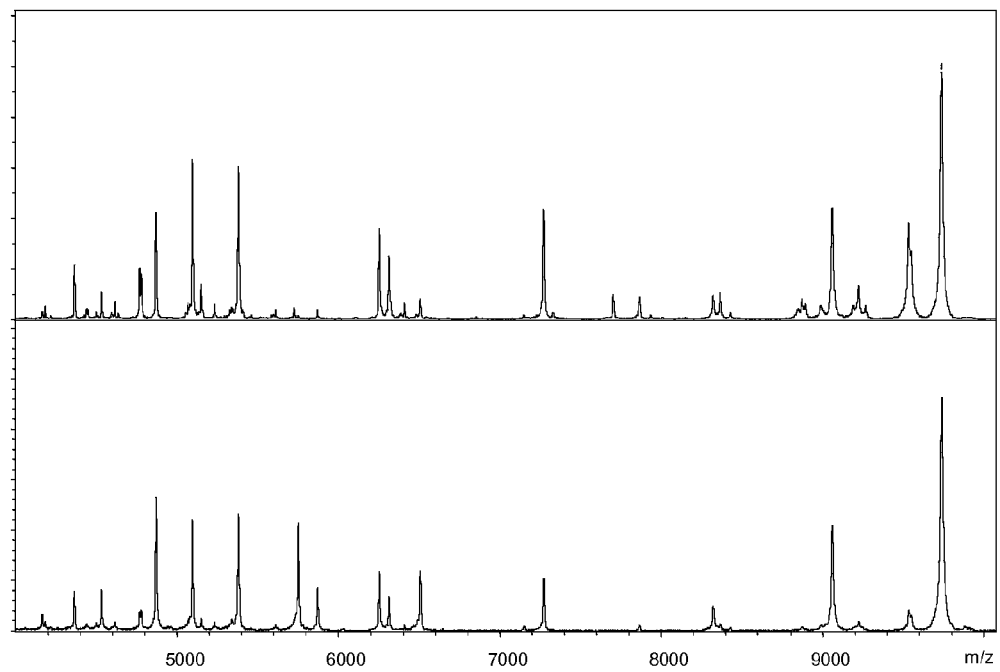
FIG. 1 shows two mass spectra with protein profiles of *Escherichia coli*: the mass spectrum at the top is from a non-resistant type whereas the *E. coli* in the mass spectrum at the bottom has a resistance to ampicillin due to a plasmid pUC19. The mass spectra contain predominantly protein signals of the same mass, with the usual lack of reproducibility of the intensities. They are identified as being identical by suitable computer programs.
Figure 2:
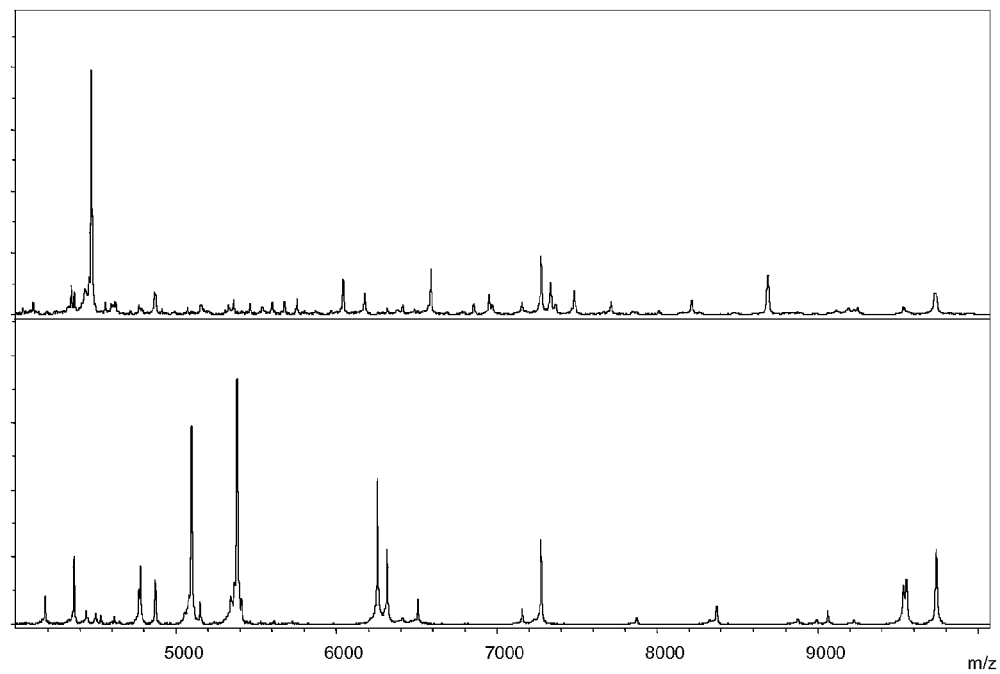
FIG. 2 shows the protein profiles of the non-resistant (top) and resistant (bottom) *E. coli* from FIG. 1 except that, in this case, ampicillin in a liquid nutrient medium has been allowed to act for two hours. The non-resistant type of *E. coli* (top) has been destroyed; all protein signals of the mass spectra from FIG. 1 have disappeared. The resistant type (bottom) produces a protein profile which is sufficiently similar to the two mass spectra in FIG. 1.

The destruction of the microbes is immediately visible in the mass spectrum because the mass spectrum now bears no similarity whatsoever to the microbe spectra of the living microbes. Such a case is shown in FIGS. 1 and 2 for E. coli under the effect of ampicillin. The proteins of the microbes are lost because the centrifuging precipitates only the membrane sheaths in the main. Most antibiotics completely destroy the microbes.

When the microbes are killed off leaving their cellular structure intact, and also to a certain extent when growth is inhibited, considerable changes to the internal metabolism occur. The proteases are no longer controlled and so the nucleoproteins of the ribosomes, which are present in high concentrations, and other proteins present in high concentrations, are immediately broken down. This means that the mass spectra which are measured are very different but it is quite possible that they still have several of the protein signals which are found in healthy, living microbes.

If growth is only weakly inhibited, many proteins in the microbes remain intact and can thus also be found in an unmodified state in the mass spectra. Only a few proteins have recognizable modifications: enzymatic attacks (many antibiotics are enzymes), mainly by the above-described endogenous proteases, change the mass of the proteins and so they appear in a different place in the mass spectrum. It is much more difficult to identify the resistance in this case than it is with microbes which have been completely destroyed. The dead or growth-inhibited microbes now generally have weakened membranes, however, so that other substances which would normally not have a damaging effect on the microbes can now penetrate into the microbes and bring about characteristic modifications, for example digestion of the proteins. One embodiment of the invention is therefore to add other attacking substances to the nutrient medium at the same time as the antibiotics, for example digestion enzymes such as proteases.

A lack of growth due to the effect of the antibiotics can also be determined in other ways. One option is to add substances to the nutrient media which make it possible to differentiate mass spectrometrically between newly grown and growth-inhibited microbes. It is possible, for example, to add isotope-marked nutrients which bring about a characteristic modification of the mass profile of the proteins in living and growing microbes. All amino acids in the nutrient media can be marked with the $^{15}N$ isotope of nitrogen, for example. If the growth of the microbes is inhibited and they absorb no nutrients, this is immediately identified mass spectrometrically because the characteristic mass increases brought about by $^{15}N$ are absent. It is also possible to undertake other types of derivatization of nutrients from the nutrient media, however.

Nutrients are known whose derivates are taken up fully by microbes into the metabolism instead of the original nutrients, thus forming products of different mass.

Moreover, a lack of growth can also be clarified by quantitative growth comparisons. If it is not possible to differentiate between the protein profiles of inhibited and normal microbes, then the addition of the same quantity of reference microbes of a similar type and the use of a quantitative reference measurement can serve to identify growth-inhibited or even dead microbes, but not those which are lyzed. It is preferable if the reference microbes are resistant and that they grow normally; if necessary, non-resistant microbes can also be used, however. The mass spectra of the two types of microbe are superimposed roughly 1:1 if both types of microbe are present in the sample preparation in equal quantities. In two hours, the difference between the number of non-growing and growing microbes has increased by at least a factor of 10 and so it is possible to identify growth-inhibited microbes by how many of them are present in the mass spectrum. It is even possible to identify growth-inhibited microbes when their growth is not completely inhibited but they merely grow significantly more slowly than resistant strains. An advance identification can provide information as to whether such semi-resistant types of microbe may be present.

The method can be used on several portions of the nutrient medium which are used in parallel and supplied with different types of antibiotic in such a way that several types of resistance can be measured at the same time, for example in microtitration plates which can also be centrifuged. In this case it is advisable to allow the microbes to grow in one of the microvessels without antibiotics being added in order to obtain reference mass spectra of these microbes.

Responsible hospitals generally only use between three and a maximum of five antibiotics on a regular basis, with some five further antibiotics on hand for cases of resistance, so that only the resistances to about ten antibiotics have to measured on a regular basis.

With knowledge of the invention, the methods described here can be modified by those skilled in the art in a wide variety of ways. Some of these modifications have already been described above; there are certainly further methods which, on the fundamental basis of a brief cultivation, can generate the desired informative mass spectra of the microbes with information about their resistances.

What is claimed is:

1. A method for determining the resistance of microbes to a specific antibiotic, comprising:
   (a) cultivating a first quantity of the microbes in a nutrient medium containing the antibiotic;
   (b) cultivating a second quantity of the microbes using the same nutrient medium and cultivation conditions used in step (a) except that the nutrient medium does not contain the antibiotic;
   (c) preparing a first sample from the microbes cultivated in step (a) using whole microbes or proteins extracted from the microbes;
   (d) preparing a second sample from the microbes cultivated in step (b) using whole microbes or proteins extracted from the microbes;
   (e) measuring a first mass spectrum of the first sample that is indicative of the soluble proteins of the microbes cultivated in step (a);
   (f) measuring a second mass spectrum of the second sample that is indicative of the soluble proteins of the microbes cultivated in step (b);
   (g) comparing the first and second mass spectra; and
   (h) determining the resistance of the microbes based on the comparison of step (g), wherein similarity of the spectra indicates resistance.

2. The method of claim 1, wherein the nutrient medium is a liquid nutrient medium.

3. The method of claim 2, wherein the liquid nutrient medium is contained in a microvessel of a microtitration plate.

4. The method of claim 2, further comprising removing the first and second samples of the microbes from the nutrient medium by filtration or centrifuging.

5. The method of claim 1, wherein nutrient medium used in step (a) contains reactive substances that can reactively modify microbes which are weakened by the antibiotic.

6. The method of claim 5, wherein the reactive substances are enzymes.

7. The method of claim 1, wherein the nutrient medium used in step (a) and in step (b) contains marked nutrients whose intake by the microbes can be detected mass spectrometrically.

8. The method of claim 7 wherein the marked nutrients are substances marked with isotopes.

9. A method for determining the resistance of microbes having a known mass spectrum to a specific antibiotic, comprising:
   (a) adding a quantity of the microbes and a quantity of reference microbes to a single nutrient medium that contains a quantity of the antibiotic, the reference microbes having a known mass spectrum and being of a type similar to the microbes but resistant to the antibiotic;
   (b) incubating the microbes and reference microbes in the single nutrient medium at a predetermined temperature for a predetermined time;
   (c) removing the microbes and the reference microbes from the single nutrient medium;
   (d) applying the removed microbes, the removed reference microbes and a matrix solution to a mass spectrometric sample support and drying the matrix solution on the sample support to produce a sample;
   (e) acquiring a mass spectrum of the sample; and
   (f) determining the microbes to be resistant to the antibiotic if the acquired mass spectrum is substantially a superposition of the known mass spectrum of the microbes and the known mass spectrum of the reference microbes.

* * * * *